(12) United States Patent
Miller (10) Patent No.: US 8,430,819 B2
(45) Date of Patent: Apr. 30, 2013

(54) SYSTEM AND METHOD FOR ULTRASOUND IMAGING WITH A CONFIGURABLE RECEIVE APERTURE

(75) Inventor: Steven Charles Miller, Phoenix, AZ (US)

(73) Assignee: General Electric Company, Schenectady, NY (US)

( * ) Notice: Subject to any disclaimer, the term of this patent is extended or adjusted under 35 U.S.C. 154(b) by 411 days.

(21) Appl. No.: 12/790,185

(22) Filed: May 28, 2010

(65) Prior Publication Data

US 2011/0295122 A1    Dec. 1, 2011

(51) Int. Cl.
*A61B 8/00* (2006.01)
(52) U.S. Cl.
USPC ............ 600/447; 600/407; 600/437; 600/443
(58) Field of Classification Search .................. 600/407, 600/437, 447, 459; 370/270
See application file for complete search history.

(56) References Cited

U.S. PATENT DOCUMENTS

| 5,897,501 | A  | * | 4/1999 | Wildes et al. | 600/447 |
| 6,524,254 | B2 | * | 2/2003 | Erikson | 600/447 |
| 6,676,602 | B1 | * | 1/2004 | Barnes et al. | 600/443 |
| 2007/0016026 | A1 | * | 1/2007 | Thomenius et al. | 600/437 |
| 2007/0161899 | A1 | * | 7/2007 | Barnes et al. | 600/447 |

* cited by examiner

*Primary Examiner* — James Kish
*Assistant Examiner* — Michael N Fisher (57) ABSTRACT

A system and method of ultrasound imaging includes a beamformer including a plurality of channels, a two-dimensional transducer array including a plurality of elements, and a plurality of signal pathways linking the plurality of elements to the plurality of channels. The system and method also include a plurality of switches positioned along the plurality of signal pathways. The plurality of switches being configured to actively connect a subset of the plurality of elements to the plurality of channels in order to form a receive aperture. The plurality of switches are further configured to control an aspect ratio of the receive aperture by changing which of the plurality of elements are actively connected to the plurality of channels.

19 Claims, 8 Drawing Sheets

SYSTEM AND METHOD FOR ULTRASOUND IMAGING WITH A CONFIGURABLE RECEIVE APERTURE

FIELD OF THE INVENTION

This disclosure relates generally to ultrasound imaging and specifically to a two-dimensional ultrasound transducer array with a configurable receive aperture.

BACKGROUND OF THE INVENTION

A conventional ultrasound imaging system comprises an array of ultrasonic transducer elements for transmitting an ultrasound beam and receiving a reflected beam from the object being studied. By selecting the time delay (or phase) and amplitude of the applied voltages, the individual elements can be controlled to produce ultrasonic waves which combine to form a net ultrasonic wave that travels along a preferred vector location and direction and is focused at a selected point along the beam. Multiple firings may be used to acquire data representing the same anatomical information. The beamforming parameters of each of the firings may be varied to provide a change in maximum focus or otherwise change the content of the received data for each firing, e.g., by transmitting successive beams along the same scan line with the focal point of each beam being shifted relative to the focal point of the previous beam. By changing the time delay and amplitude of the applied voltages, the beam with its focal point can be moved in a plane to scan the object.

The same principles apply when the transducer array is employed to receive the reflected sound energy. The voltages produced at the receiving elements are summed so that the net signal is indicative of the ultrasound reflected from points in the object. As with the transmission mode, this focused reception of the ultrasonic energy is achieved by imparting a separate time delay (and/or phase shift) and gain to the signal from each receiving element. The receive delays may be modified during reception to dynamically increase the focal depth as echoes are received from progressively deeper points along a line within the transmit beam.

Recently, many conventional ultrasound imaging systems have included a two-dimensional transducer array (hereinafter a 2D transducer array). The 2D transducer array typically comprises a number of transducer elements arranged in a grid. By controlling the timing and amplitude of the elements in the 2D transducer array, it is possible to steer and translate the transmitted ultrasound beam in both an azimuth direction and in an elevation direction. The use of a 2D transducer array allows the ultrasound transducer or probe to have greater flexibility and it enables greater accuracy in the acquisition of volumetric data.

However, for some ultrasound systems and probes, the number of transducer elements exceeds the number of channels in the console beamformer electronics or the number of channels supported by the console interface. For example, a 2D transducer array used for 3D and 4D imaging may require a very high number of elements, roughly the square of the number of elements needed for a 1D array used for 2D imaging. For example, a linear array which would required 128 to 192 elements for 2D imaging would need approximately 8,000 to 10,000 elements for 3D and 4D imaging. In cases like this, one or more probe beamforming and/or switching circuits may be used to dynamically couple the available channels to different subsets of transducer elements during different portions of the image formation process. Even if a probe beamforming circuit, also known as a sub-aperture processor (SAP), is used to combine 10 or more elements for each console beamformer channel, there may still not be enough console beamformer channels to utilize all of the elements in the 2D transducer array.

Additionally, while scanning a single slice, such as for a 2D display, it is often desirable to optimize the resolution within the slice. One way to optimize the resolution is to use a receive aperture that has its widest extent in the scanning dimension. For example, when scanning in the azimuth direction, it may be desirable to have a receive aperture that is widest in the azimuth direction. Likewise, when scanning in the elevation direction, it may be desirable to have a receive aperture that is widest in the elevation direction. Additionally, when scanning a volume to render as a 3D or 4D image, it may be desirable to optimize the resolution for more uniformity in both scanning dimensions by using an aperture that is shaped more like a square. For these and other reason, there is a need for an easily configurable ultrasound imaging system with the flexibility to optimize the shape of the receive aperture of a 2D transducer array based on the type of image that is desired.

BRIEF DESCRIPTION OF THE INVENTION

The above-mentioned shortcomings, disadvantages and problems are addressed herein which will be understood by reading and understanding the following specification.

In an embodiment, an ultrasound imaging system includes a beamformer including a plurality of channels. The ultrasound imaging system includes a two-dimensional transducer array including a plurality of elements, the plurality of elements exceeding the plurality of channels. The ultrasound imaging system includes a plurality of signal pathways, each signal pathway linking one of the plurality of elements to one of the plurality of channels. The ultrasound imaging system also includes a plurality of switches positioned along the plurality of signal pathways. The plurality of switches are configured to actively connect a subset of the plurality of elements to the plurality of channels in order to form a receive aperture. The plurality of switches are further configured to control an aspect ratio of the receive aperture by changing which of the plurality of elements are actively connected to the plurality of channels.

In another embodiment, an ultrasound imaging system with a configurable receive aperture includes a beamformer including a plurality of channels. The ultrasound imaging system includes a two-dimensional transducer array comprising a plurality of elements, the plurality of elements exceeding the plurality of channels. Each of the elements is electrically associated with one of the channels in a two-dimensional pattern. The two-dimensional pattern includes a first sub-pattern of two-dimensional channel assignments and a second sub-pattern of two-dimensional channel assignments. The ultrasound imaging system includes a plurality of switches configured to control which of the plurality of elements are actively connected to the plurality of channels. The plurality of switches and the two-dimensional pattern are adapted to enable a first subset of the plurality of elements to be actively connected to the plurality of channels in order to form a first receive aperture with a first aspect ratio. The plurality of switches and the two-dimensional pattern are further adapted to enable a second subset of the plurality of elements to be actively connected in order to form a second receive aperture with a second aspect ratio.

In another embodiment, a method of ultrasound imaging includes grouping elements of a two-dimensional transducer array into a plurality of sub-apertures and assigning each of the plurality of sub-apertures to a channel from the beamformer in a two-dimensional pattern. The method includes connecting a first subset of the plurality of sub-apertures to the channels from the beamformer according to the channel assignments in the two-dimensional pattern to form a first receive aperture with a first aspect ratio. The method also includes connecting a second subset of the plurality of sub-apertures to the channels from the beamformer according to the channel assignments in the two-dimensional pattern to form a second receive aperture with a second aspect ratio.

Various other features, objects, and advantages of the invention will be made apparent to those skilled in the art from the accompanying drawings and detailed description thereof.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
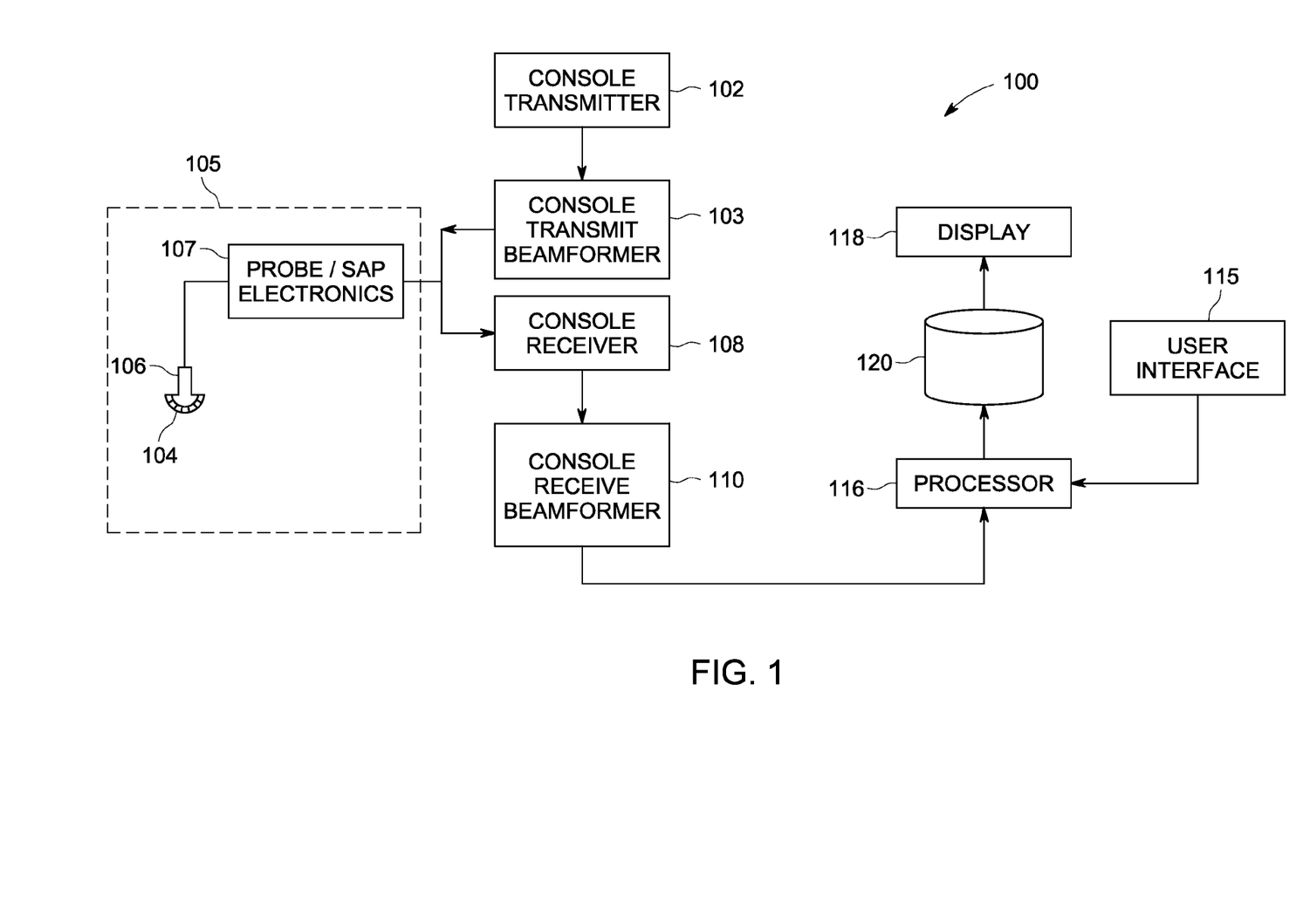
FIG. 1 is a schematic diagram of an ultrasound imaging system in accordance with an embodiment.

FIG. 1 is a schematic diagram of an ultrasound imaging system 100. The ultrasound imaging system 100 includes a console transmitter 102 that transmits a signal to a console transmit beamformer 103 which in turn drives elements 104 within a transducer array 106 to emit pulsed ultrasonic signals into a structure, such as a patient (not shown). A probe assembly 105 includes the transducer array 106, the elements 104 and probe/SAP electronics 107. The probe/SAP electronics 107 may be used to control the switching of the elements 104. The probe/SAP electronics 107 may also be used to group the elements 104 into one or more sub-apertures. A variety of geometries of transducer arrays may be used. The pulsed ultrasonic signals are back-scattered from structures in the body, like blood cells or muscular tissue, to produce echoes that return to the elements 104. The echoes are converted into electrical signals, or ultrasound data, by the elements 104 and the electrical signals are received by a console receiver 108.

For purposes of this disclosure, the term ultrasound data may include data that was acquired and/or processed by an ultrasound system. The electrical signals representing the received echoes are passed through a console receive beamformer 110 that outputs ultrasound data. A user interface 115 may be used to control operation of the ultrasound imaging system 100, including, to control the input of patient data, to change a scanning or display parameter, and the like.

The ultrasound imaging system 100 also includes a processor 116 to process the ultrasound data and prepare frames of ultrasound information for display on a display 118. The processor 116 may be adapted to perform one or more processing operations according to a plurality of selectable ultrasound modalities on the ultrasound information. The ultrasound information may be processed in real-time during a scanning session as the echo signals are received. For the purposes of this disclosure, the term "real-time" is defined to include a procedure that is performed without any intentional delay. Additionally or alternatively, the ultrasound information may be stored temporarily in a buffer (not shown) during a scanning session and processed in less than real-time in a live or off-line operation. Some embodiments of the invention may include multiple processors (not shown) to handle the processing tasks. For example, a first processor may be utilized to demodulate and decimate the ultrasound signal while a second processor may be used to further process the data prior to displaying an image. It should be appreciated that other embodiments may use a different arrangement of processors.

Still referring to FIG. 1, the ultrasound imaging system 100 may continuously acquire ultrasound information at a frame rate of, for example, 20 Hz to 30 Hz. However, other embodiments may acquire ultrasound information at a different rate. For example, some embodiments may acquire ultrasound information at a frame rate of over 100 Hz depending on the intended application. A memory 120 is included for storing processed frames of acquired ultrasound information that are not scheduled to be displayed immediately. In an exemplary embodiment, the memory 120 is of sufficient capacity to store at least several seconds worth of frames of ultrasound information. The frames of ultrasound information are stored in a manner to facilitate retrieval thereof according to its order or time of acquisition. The memory 120 may comprise any known data storage medium.

Optionally, embodiments of the present invention may be implemented utilizing contrast agents. Contrast imaging generates enhanced images of anatomical structures and blood flow in a body when using ultrasound contrast agents including microbubbles. After acquiring ultrasound data while using a contrast agent, the image analysis includes separating harmonic and linear components, enhancing the harmonic component and generating an ultrasound image by utilizing the enhanced harmonic component. Separation of harmonic components from the received signals is performed using suitable filters. The use of contrast agents for ultrasound imaging is well-known by those skilled in the art and will therefore not be described in further detail.

In various embodiments of the present invention, ultrasound information may be processed by other or different mode-related modules (e.g., B-mode, Color Doppler, power Doppler, M-mode, spectral Doppler anatomical M-mode, strain, strain rate, and the like) to form 2D or 3D data sets of image frames and the like. For example, one or more modules may generate B-mode, color Doppler, power Doppler, M-mode, anatomical M-mode, strain, strain rate, spectral Doppler image frames and combinations thereof, and the like. The image frames are stored and timing information indicating a time at which the image frame was acquired in memory may be recorded with each image frame. The modules may include, for example, a scan conversion module to perform scan conversion operations to convert the image frames from Polar to Cartesian coordinates. A video processor module may be provided that reads the image frames from a memory and displays the image frames in real time while a procedure is being carried out on a patient. A video processor module may store the image frames in an image memory, from which the images are read and displayed.

Figure 2:
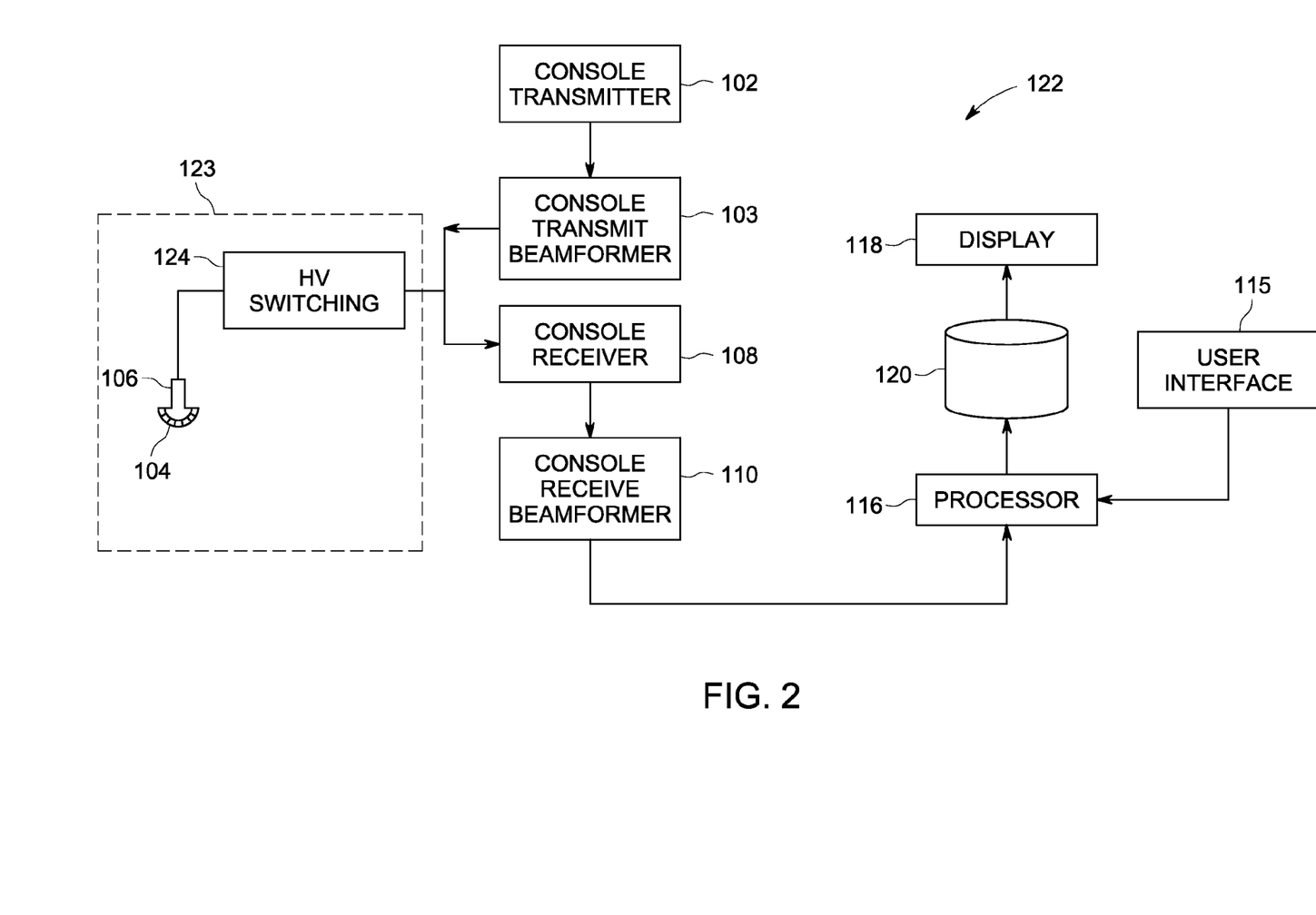
FIG. 2 is a schematic diagram of an ultrasound imaging system in accordance with an embodiment.

Referring to FIG. 2, a schematic diagram of an ultrasound imaging system 122 is shown in accordance with an embodiment. Elements of the ultrasound imaging system 122 that are the same as elements from the ultrasound imaging system 100 shown in FIG. 1 will be labeled with common reference numbers and will not be described in detail. In the ultrasound imaging system 122, a probe assembly 123 includes a high-voltage switching assembly 124 connected to the transducer array 106 and the elements 104. The high-voltage switching assembly 124 allows the probe assembly 123 to use a common circuit (not shown) for both transmit and receive functions.

Figure 3:
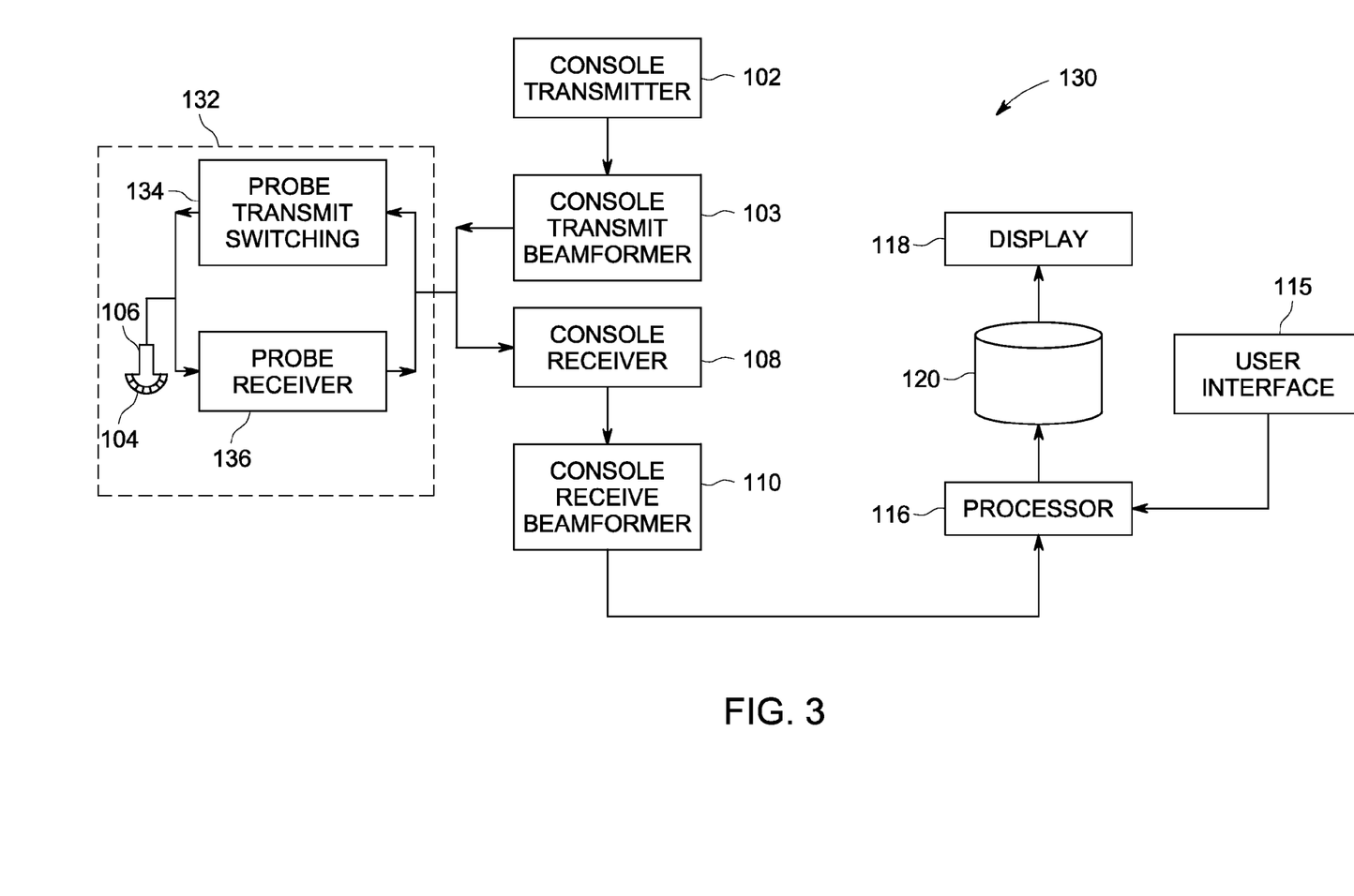
FIG. 3 is a schematic diagram of an ultrasound imaging system in accordance with an embodiment.

Referring to FIG. 3, a schematic diagram of an ultrasound imaging system 130 is shown in accordance with an embodiment. Elements of the ultrasound imaging system 130 that are the same as elements from the ultrasound imaging system 100 shown in FIG. 1 and the ultrasound imaging system 122 shown in FIG. 2 will be labeled with common reference numbers and will not be described in detail. The ultrasound imaging system 130 includes a probe assembly 132 comprising a probe transmit switching assembly 134 and a probe receiver 136. According to an embodiment, the probe transmit switching assembly 134 may be used in place of the console transmitter 102 to generate an ultrasound transmit signal. It should be appreciated by those skilled in the art that the probe transmit switching assembly 134 may perform a beamforming function according to some embodiments. Additionally the probe receiver 136 may receive and provide beamforming for the received signal in place of, or in addition to, the console receive beamformer 110 in other embodiments.

Figure 4:
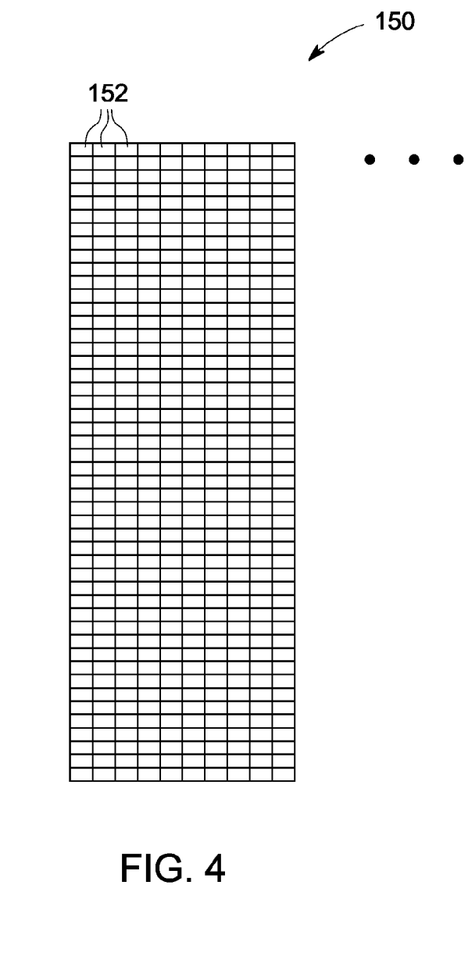
FIG. 4 is a schematic representation of a two-dimensional transducer array in accordance with an embodiment.

Referring to FIG. 4, a schematic representation of a two-dimensional (2D) transducer array is shown in accordance with an embodiment. The 2D transducer array 150 may be connected to an ultrasound imaging system such as the ultrasound imaging system 100 shown in FIG. 1. The 2D ultrasound array comprises a plurality of elements 152. According to an embodiment, there may be 7680 elements arranged into 160 columns and 48 rows. The schematic representation of the 2D transducer array shows all 48 rows, but it includes only a small number of the columns for clarity. The 48 rows run in an elevation direction and the 160 columns run in an azimuth direction. For purposes of the figures within this disclosure, the azimuth direction will be defined to include an x-direction and the elevation direction will be defined to include a y-direction.

Figure 5:
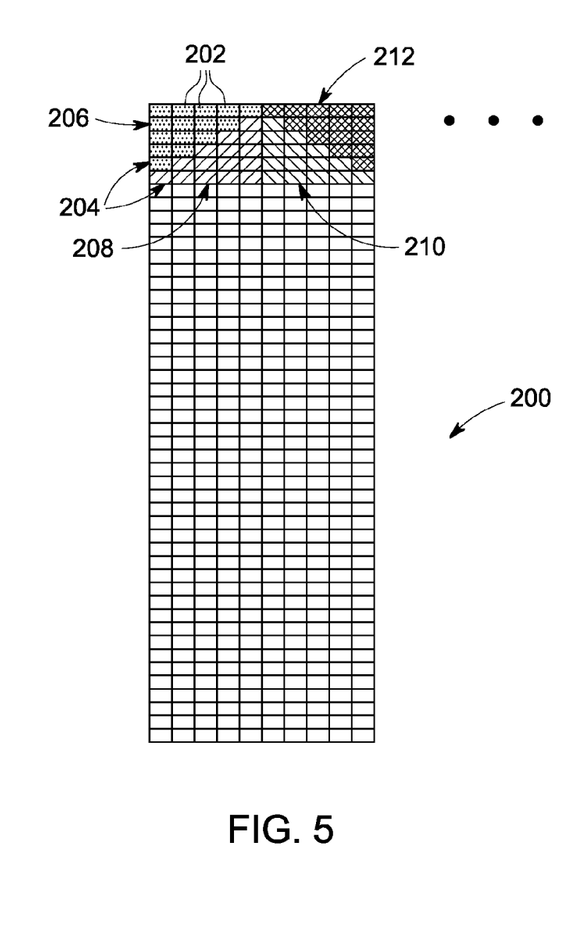
FIG. 5 is a schematic representation of a two-dimensional transducer array in accordance with an embodiment.

Referring to FIG. 5, a schematic representation of a 2D transducer array is shown in accordance with an embodiment. The 2D transducer array 200 comprises a plurality of elements 202 arranged into 160 columns and 48 rows in a manner similar to the embodiment described with respect to FIG. 4. However, the elements 202 are further grouped into a plurality of sub-apertures 204. According to an embodiment, each of the sub-apertures 204 comprises 15 elements arranged in a generally triangular shape. For example, a first sub-aperture 206 is indicated with stippling, a second sub-aperture 208 is indicated with //-hatching, a third sub-aperture 210 is indicated by \\-hatching, and a fourth sub-aperture 212 is indicated by cross-hatching. Only four of the sub-apertures are indicated in FIG. 5. However, it should be appreciated by those skilled in the art that all of the elements may be arranged into sub-apertures in a manner consistent with the first sub-aperture 206, the second sub-aperture 208, the third sub-aperture 210, and the fourth sub-aperture 212. According to an embodiment, the elements that comprise a sub-aperture may each have a relative timing or phase offset that enables each sub-aperture to focus in an independent direction if desired. However, each of the sub-apertures 204 may be configured to output its signal to a single beamformer channel in order to minimize the total number of channels needed for a given number of elements 202. According to an embodiment, all of the plurality of elements 202 may be arranged into 15-element sub apertures. For example, the elements 202 of the transducer array 200 may be arranged into 8 rows of 48 sub apertures. In FIG. 5, only the first four of the sub-apertures are indicated. It should be appreciated by those skilled in the art that in other embodiments the transducer elements may be arranged into sub-apertures that are different from those depicted in FIG. 5. For example, embodiments may by configured with sub-aperture processing configured to create sub-apertures with shapes including a square, a rectangular, or a diamond. It should also be appreciated that other embodiments may not employ sub-aperture processing. For embodiments without sub-aperture processing, the each of the elements may be directly connected to a single beamformer channel.

Figure 6:
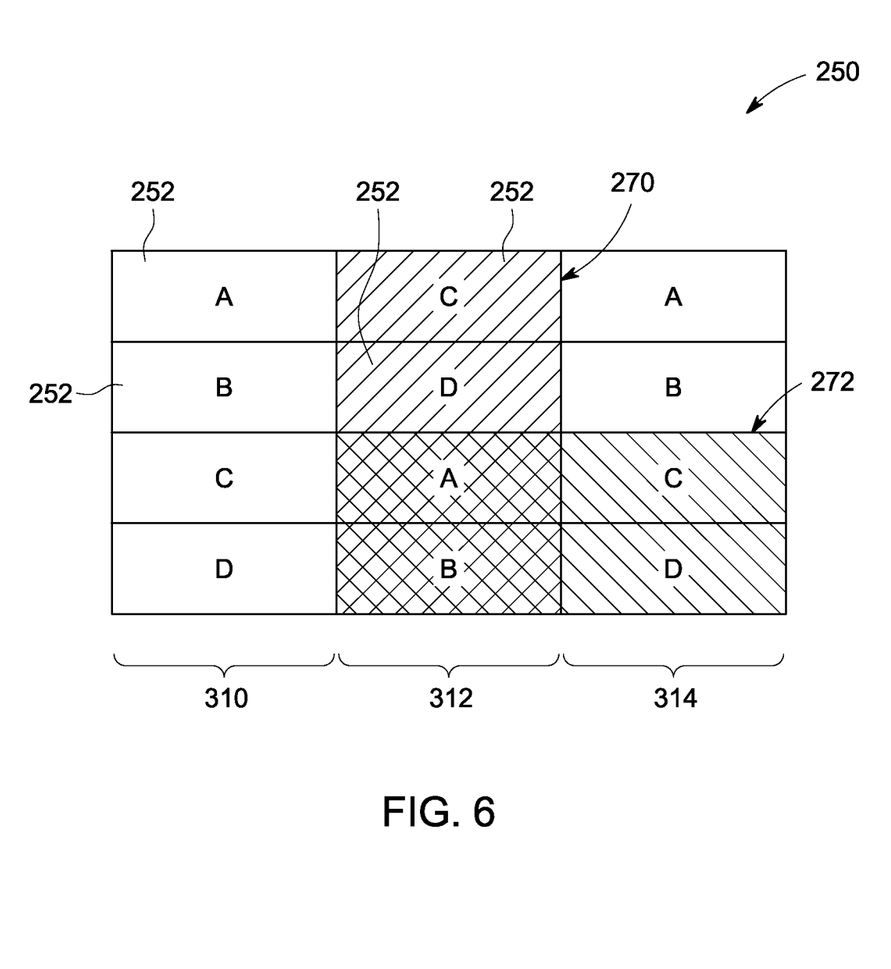
FIG. 6 is a schematic representation of a two-dimensional pattern showing channel assignments for a two-dimensional transducer array in accordance with an embodiment.

Referring to FIG. 6, a schematic representation of a two-dimensional pattern showing element to channel assignments for a two-dimensional transducer array is shown according to an embodiment. The two-dimensional pattern 250 includes a plurality of sub-patterns 252. The letters A, B, C, and D are used to indicate each of the four unique sub-patterns in the two-dimensional pattern 250. Each of the sub-patterns represents a fixed spatial arrangement of channel assignments. For example, the sub-pattern A represents a fixed spatial arrangement of channel assignments. According to an embodiment, each of the channel assignments within the sub-pattern may represent a signal pathway linking one or more elements to a beamformer channel. Additional description of the signal pathways will be provided hereinafter.

Figure 7:
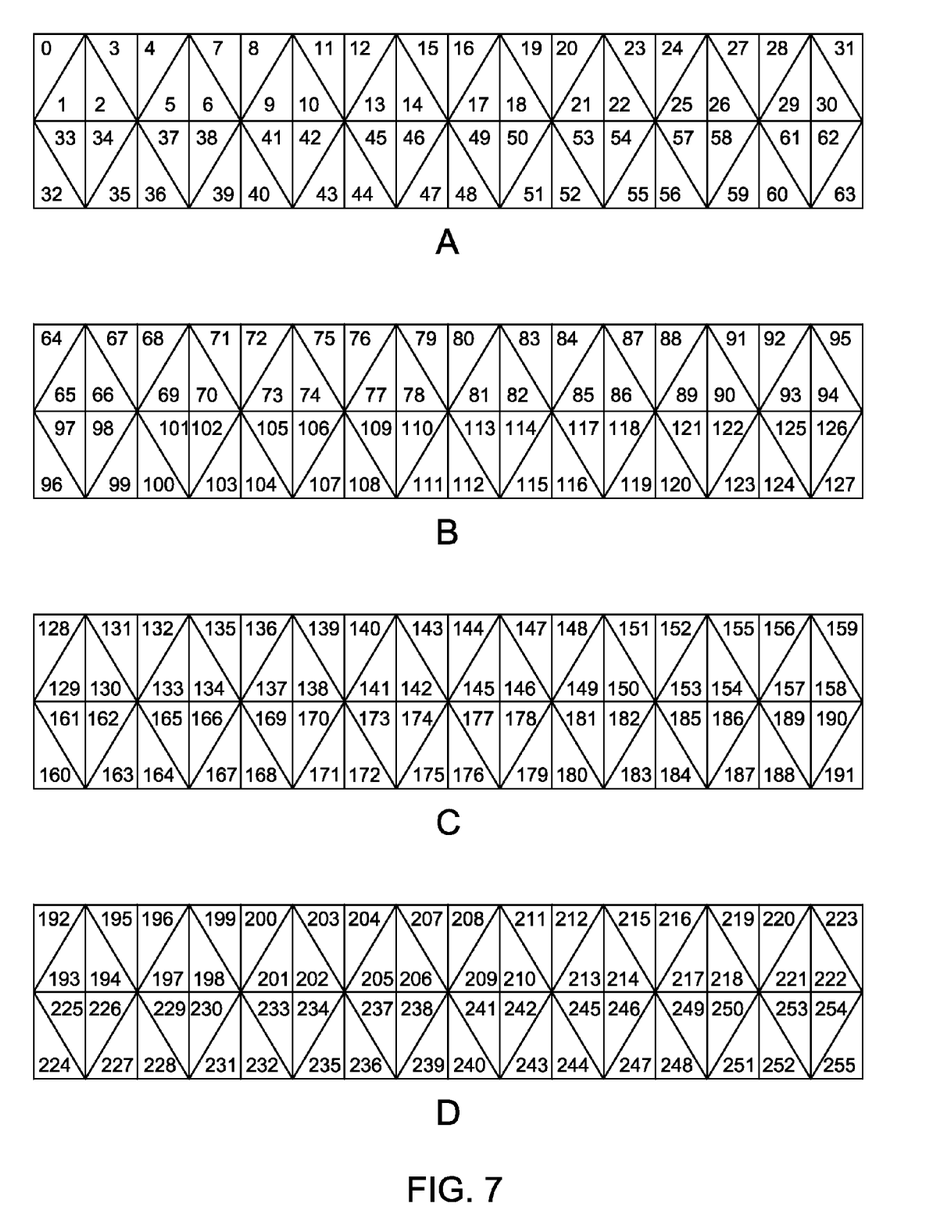
FIG. 7 is a schematic representation of four sub-patterns in accordance with an embodiment.

Referring to FIG. 7, a schematic representation of multiple sub-patterns is shown in accordance with an embodiment. A first sub-pattern A, a second sub-pattern B, a third sub-pattern C, and a fourth sub-pattern D each represent a pattern of linking transducer array elements to beamformer channels. The sub-patterns A, B, C, and D may be used with a transducer array such as the transducer array 200 (shown in FIG. 3). According to an embodiment, the beamformer 110 (shown in FIG. 1) may have 256 channels. The transducer array 200 has 7680 elements arranged into 512 sub-apertures 204 (shown in FIG. 5). According to an embodiment, each of the sub-apertures 204 is linked to one of the beamformer channels. Details of the linking between the sub-apertures 204 and the beamformer channels will be discussed in detail hereinafter.

The first sub-pattern A shows one way that sub-apertures may be linked to beamformer channels in a two-dimensional pattern. In FIG. 7, each of the triangular shapes represents a sub-aperture. The numbers 0-63 correspond to the channels to which each of the sub-apertures are linked. For example, a sub-aperture 258 is linked to channel 0 while a sub-aperture 260 is linked to channel 44.

The second sub-pattern B 252 shows a two-dimensional pattern linking sub-apertures to channels 64 to 127. The third sub-pattern C shows a fixed two-dimensional pattern linking sub-apertures to channels 128-191. The fourth sub-pattern D shows a fixed two-dimensional pattern linking sub-apertures to channels 192-255. According to the embodiment shown in FIG. 7, the sub-apertures are linked to beamformer channels in ascending order starting at the upper left and rastering through the subsequent rows. The sub-apertures of other embodiments may be linked to the beamformer channels in other patterns in accordance with other embodiments.

Referring now to FIGS. 6 and 7. FIG. 6 shows the first sub-pattern A, the second sub-pattern B, the third sub-pattern C, and the fourth sub-pattern D arranged in a two-dimensional pattern 250. According to an embodiment, the two-dimensional pattern 250 contains each of the sub-patterns repeated three times. For example, the first sub-pattern A is repeated three times in the two-dimensional pattern 250. The first sub-pattern A is the same in each of the three locations within the two-dimensional pattern 200. Sub-pattern B, sub-pattern C, and sub-pattern D are also each repeated three times within the two-dimensional pattern 250.

The two-dimensional pattern 250 represents the channel assignments of all of the elements in a two-dimensional array. Each location within the two-dimensional pattern 250 corresponds with a portion of a two-dimensional transducer array. The two-dimensional pattern 250 includes information about the way the elements of the transducer array are linked to the beamformer channels. Based on the exemplary embodiment shown in FIGS. 6 and 7, four unique sub-patterns are used to represent all of the beamformer channels. In order to form a receive aperture using all of the beamformer channels, it is therefore necessary to use elements from at least the first sub-pattern A, the second sub-pattern B, the third sub-pattern C, and the fourth sub-pattern a The sub-patterns 252 are arranged in an alternating manner in the two-dimensional pattern 250. For the purposes of this disclosure, the term "alternating manner" is defined to include patterns where each sub-pattern is either adjacent to the edge of the transducer array or to a different sub-pattern. In other words, in a two-dimensional pattern where the sub-patterns are arranged in an alternating manner, each sub-pattern is next to either a sub-pattern of a different configuration or an edge of the transducer array. A two-dimensional pattern with the sub-patterns arranged in an alternating manner would not include two of the same sub-patterns positioned next to each other.

Referring to FIG. 6, a first receive aperture 270 is shown. The first receive aperture 270 is indicated with //-hatching. A second receive aperture 272 is also shown. The second receive aperture 272 is indicated with \\-hatching. Elements within two of the sub-patterns are used in both the first receive aperture 270 and the second receive aperture 272. The portion of the two-dimensional pattern 250 corresponding to elements used in both the first receive aperture 270 and the second receive aperture 272 is indicated with cross-hatching.

Figure 8:
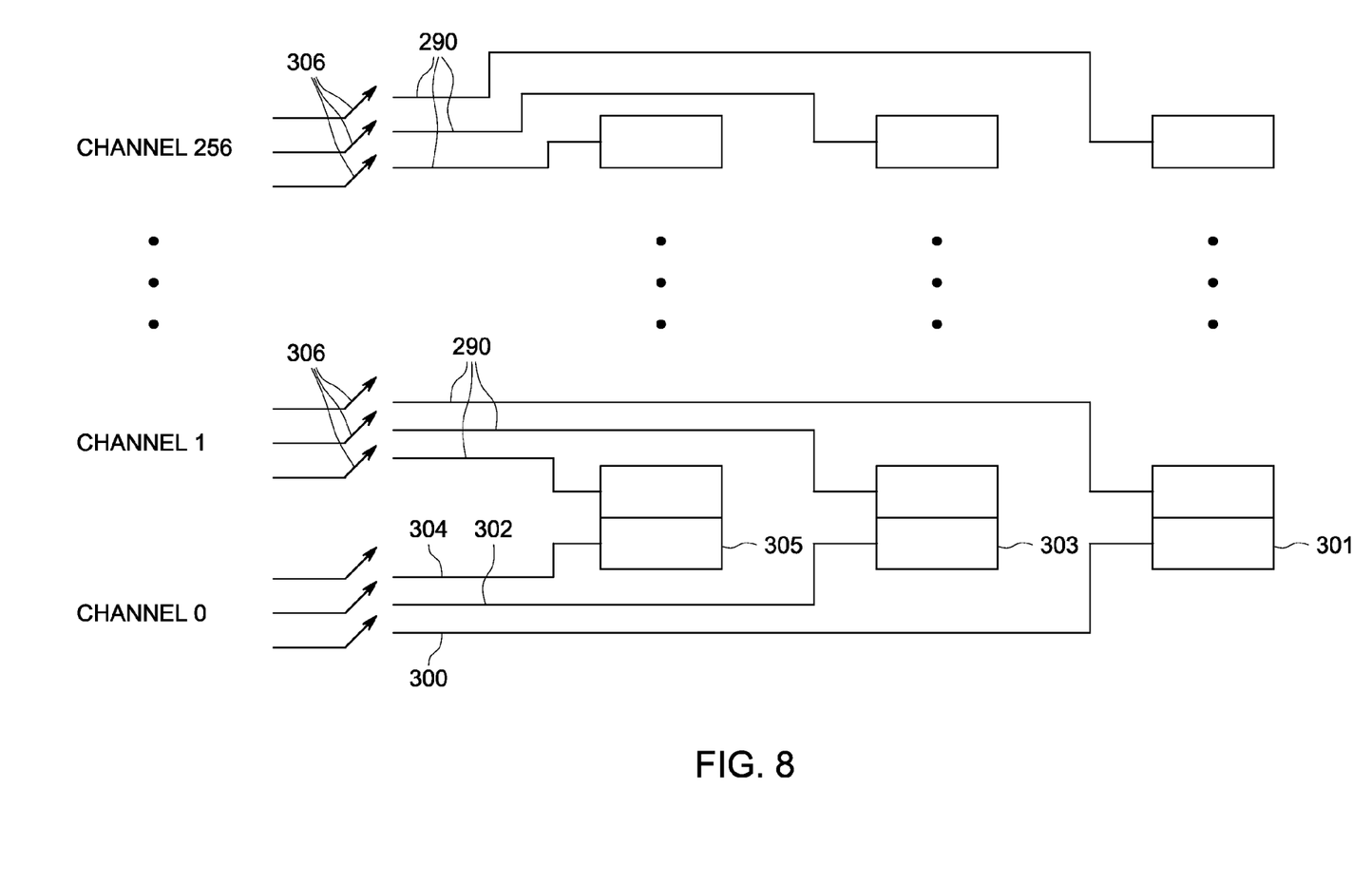
FIG. 8 is a schematic representation of signal pathways linking sub-apertures to channels in accordance with an embodiment.

Referring to FIG. 8, a schematic representation of signal pathways linking sub-apertures to channels is shown in accordance with an embodiment. There are a plurality of signal pathways 290 linking three sub-apertures to each channel according to an embodiment. For example, a first signal pathway 300 links channel 0 to sub-aperture 301, a second signal pathway 302 links channel 0 to sub-aperture 303, and a third signal pathway 304 links channel 0 to sub-aperture 305. A plurality of switches 306 is positioned along the plurality of signal pathways 290. The plurality of switches 306 control which of the sub-aperture are actively connected to the beamformer channels. For example, according to an embodiment, only one of sub-aperture 305, sub-aperture 303, and sub-aperture 301 may be connected to channel 0 at a time. According to other embodiments, the channels may be linked to individual elements instead of sub-apertures.

The plurality of signal pathways 290 and the plurality of switches 306 may be part of an integrated circuit (not shown) in accordance with an embodiment. The integrated circuit may positioned within the transducer. Each of the signal pathways 290 represents an electrical pathway linking a group of elements in a sub-aperture to a beamformer channel. According to other embodiments, each of the plurality of signal pathways may connect a single element of the transducer array to a beamformer channel.

Referring now to both FIG. 6 and FIG. 8, the sub-patterns 252 are arranged in a fixed order within all of the columns. For example, from top to bottom, all of the sub-patterns are arranged in an A-B-C-D order. In a first column 310, the sub-patterns are arranged A-B-C-D. In a second column 312, the sub-patterns are arranged C-D-A-B. The sub-patterns in the second column 312 are in the same order as in the first column, but there is an offset of 2 between the adjacent columns. In a third column 314, the sub-patterns are again arranged in A-B-C-D. There is also an offset of 2 between the second column 312 and the third column 314. It should be understood by those skilled in the art that other embodiments may use a different number of unique sub-patterns. Additionally, the two-dimensional pattern may comprise a different arrangement of the sub-patterns.

Still referring to FIG. 6 and FIG. 8, the first receive aperture 270 is longer in the elevation direction than in the azimuth direction. Conversely, the second receive aperture 272 is longer in the azimuth direction than in the elevation direction. When scanning a single slice for a two-dimensional display, it is often desirable to optimize the resolution within the slice by using a receive aperture with its widest extent in the scanning dimension. By linking channels to elements or sub-apertures as shown in FIG. 6, it is possible to have two different receive apertures, each with a different aspect ratio. For example, the first receive aperture 270 has a first aspect ratio and is configured to give a higher resolution when scanning in the elevation direction. The second receive aperture 272 has a second aspect ratio and is configured to give a higher resolution when scanning in the azimuth direction. It should be noted that according to an embodiment, it is possible to utilize all the beamformer channels with both the first receive aperture 270 and the second receive aperture 272. Additional embodiments may be configured to provide more than two different receive apertures.

Figure 9:
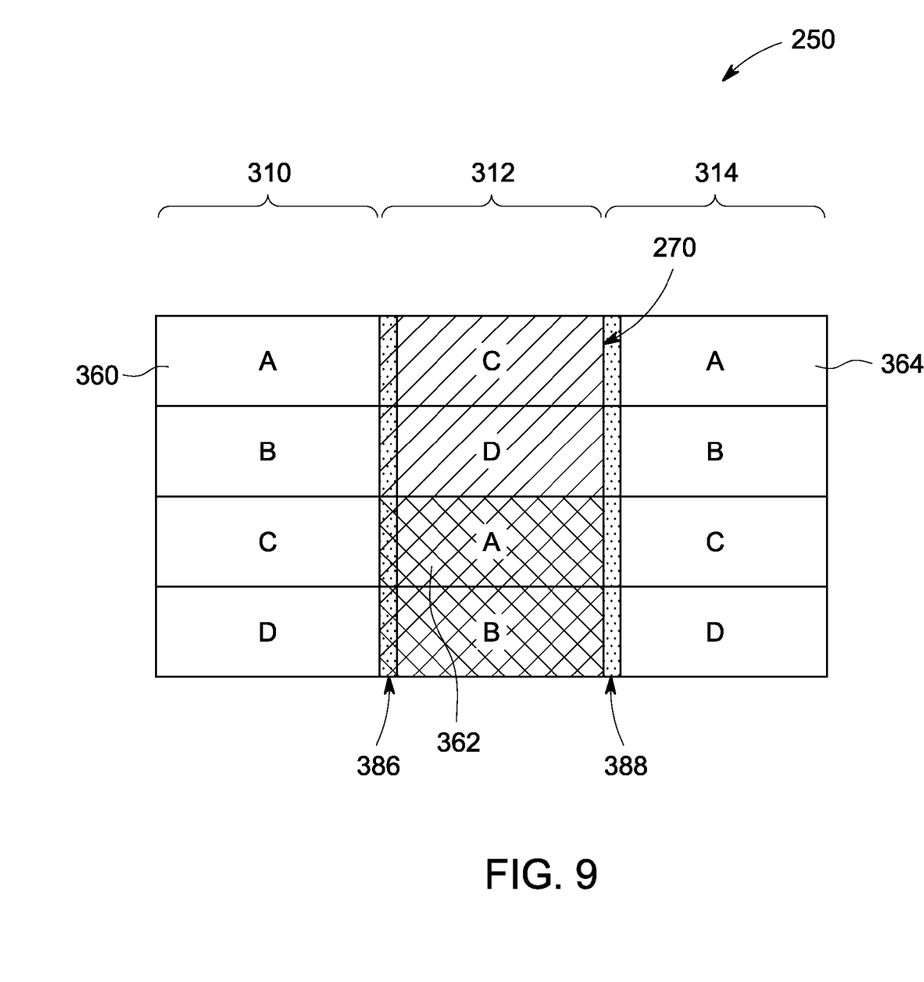
FIG. 9 is a schematic representation of a two-dimensional pattern in accordance with an embodiment.

Referring to FIG. 9, the two-dimensional pattern 250 from FIG. 6 is shown in accordance with an embodiment. Common reference numbers are used to indicate identical elements. According to an embodiment, the first receive aperture 270 may be configured to translate across the two-dimensional array. The sub-patterns of the two-dimensional pattern 250 are organized into three columns. Each of these columns includes four sub-patterns. The channels assignments for a given channel are in the same relative position within each of the common sub-patterns. For purposes of this disclosure, the term "common sub-patterns" is defined to include two or more sub-patterns with the same channel assignments in the same relative positions. Common sub-patterns are indicated with the same letter, such as A, B, C, or D within the figures of this disclosure. For example, the sub-patterns indicated by reference numbers 360, 362, and 364 are all common sub-patterns.

Still referring to FIG. 9, since the channel assignments are fixed within each of the common sub-patterns, it is possible to shift a receive aperture while utilizing all of the available beamformer channels. The first receive aperture 270 is indicated with //-hatching. Channels assigned from sub-pattern A, sub-pattern B, sub-pattern C, and sub-pattern D are actively connected to elements in the transformer array in order to form the first receive aperture 270. However, by opening a first set of switches connecting channels 386, indicated by stippling, on the left-hand side of the first receive aperture 270 and closing a second set of switches connecting channels 388, also indicated by stippling, to the right of the first receive aperture 270, it is possible translate the first receive aperture 270 to the right. Note that the sub-patterns used in the second column 312 are the same as the sub-patterns in the third column 314. As described previously, the channel assignments are the same within each of the common sub-patterns. Since the channel assignments are the same for all common sub-patterns, by turning off an element or elements associated with a given channel in one sub-pattern and turning on an element of element associated with the same channel in a common sub-pattern that is adjacent to the current receive aperture, it is possible to cause the receive aperture to translate in position. Additionally, since the same channels are used in both positions, it is possible use all of the beamformer channels for the first receive aperture 270 in both its initial position and in its translated position. In other words, if a first set of channels, such as channels 386, are disconnected from the receive aperture 270 while a second set of channels, such as channels 388 are connected, all of the same channels may be utilized in the newly-shifted receive aperture. An important aspect of this embodiment is that by arranging the sub-patterns 252 in the two-dimensional pattern 250, it is possible to translated the first receive aperture 270 in the azimuth direction while still utilizing all of the beamformer channels. It should be appreciated by those skilled in the art that it would be possible to translate the second receive aperture 272 (shown in FIG. 4) in both the azimuth direction and the elevation direction for the same reasons described hereinabove with respect to the first sub-aperture 270. It should be appreciated by those skilled in the art that while a specific two-dimensional pattern 250 was described in detail other embodiments may use a different two-dimensional pattern with either a different number or arrangement of common sub-patterns.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

I claim:

1. An ultrasound imaging system with a configurable receive aperture comprising:
   a beamformer including a plurality of channels;
   a two-dimensional transducer array comprising a plurality of elements, the plurality of elements exceeding the plurality of channels;
   a processor configured to selectively electrically connect the plurality of elements to the plurality of channels according to a two-dimensional pattern of channel assignments, the two-dimensional pattern comprising a first sub-pattern of two-dimensional channel assignments that is repeated multiple times within the two-dimensional pattern and a second sub-pattern of two-dimensional channel assignments that is repeated multiple times within the two-dimensional pattern, wherein each repetition of the first sub-pattern is configured to be non-adjacent to all other repetitions of the first sub-pattern and each repetition of the second sub-pattern is configured to be non-adjacent to all other repetitions of the second sub-pattern; and
   a plurality of switches configured to control which the plurality of elements are actively connected to the plurality of channels.

2. The ultrasound imaging system of claim 1, wherein the first sub-pattern and the second sub-pattern are arranged in an alternating manner within the two-dimensional pattern.

3. The ultrasound imaging system of claim 1, wherein the two-dimensional pattern further comprises a third sub-pattern of two-dimensional channel assignments and a fourth sub-pattern of two-dimensional channel assignments.

4. The ultrasound imaging system of claim 3, wherein the first sub-pattern, the second sub-pattern, the third sub-pattern, and the fourth sub-pattern are positioned within the two-dimensional pattern in an alternating manner.

5. The ultrasound imaging system of claim 4, wherein the sub-patterns are arranged in a plurality of rows and columns within the two-dimensional pattern.

6. The ultrasound imaging system of claim 5, wherein the sub-patterns are arranged in a fixed order in each of the plurality of rows.

7. The ultrasound imaging system of claim 6, wherein the sub-patterns are arranged in a fixed order in each of the plurality of columns.

8. The ultrasound imaging system of claim 1, wherein the plurality of switches and the two-dimensional pattern are configured to enable the first receive aperture to translate across the two-dimensional array in both an elevation direction and in an azimuth direction while using all of the plurality of channels.

9. A method of ultrasound imaging comprising:
   grouping elements of a two-dimensional transducer array into a plurality of sub-apertures;
   assigning each of the plurality of sub-apertures to a channel from a beamformer in a two-dimensional pattern, the two-dimensional pattern comprising multiple repetitions of at least two different sub-patterns of two-dimensional channel assignments, wherein the sub-patterns are arranged in a grid within the two-dimensional pattern so that adjacent sub-patterns have different channel assignments;
   With a processor:
   connecting a first subset of the plurality of sub-apertures to the channels from the beamformer according the two-dimensional pattern to form a first receive aperture with a first aspect ratio; and
   connecting a second subset of the plurality of sub-apertures to the channels from the beamformer according to the two-dimensional pattern to form a second receive aperture with a second aspect ratio.

10. The method of claim 9, wherein the two-dimensional pattern comprises at least four different sub-patterns arranged in a grid of columns and rows.

11. An ultrasound imaging system comprising:
    a beamformer including a plurality of channels;
    a two-dimensional transducer array comprising a plurality of elements, the plurality of elements exceeding the plurality of channels;
    a plurality of signal pathways, each signal pathway linking one of the plurality of elements to one of the plurality of channels;

a processor configured to establish electrical connections between the plurality of elements and the plurality of channels according to a two dimensional pattern of channel assignments, the two-dimensional pattern comprising at least two unique sub-patterns of two-dimensional channel assignments, wherein the sub-patterns are configured so that any two adjacent sub-patterns comprise different channel assignments; and a plurality of switches connected to the plurality of signal pathways, the plurality of switches configured to electrically connect a subset of the plurality of elements to the plurality of channels in order to form a receive aperture.

12. The ultrasound imaging system of claim 11, wherein the two-dimensional pattern comprises more than two unique sub-patterns of channel assignments.

13. The ultrasound imaging system of claim 11, wherein the sub-patterns are arranged in a grid of columns and rows.

14. The ultrasound imaging system of claim 13, wherein the sub-patterns are arranged in a fixed order in each of the rows.

15. The ultrasound imaging system of claim 14, wherein the sub-patterns are arranged in a fixed order in each of the columns.

16. The ultrasound imaging system of claim of claim 14, wherein the sub-patterns are arranged with an offset of one half the number of unique sub-patterns between adjacent rows.

17. The ultrasound imaging system of claim 16, wherein there are four unique sub-patterns.

18. The ultrasound imaging system of claim 17, wherein there is an offset of two unique sub-patterns in the fixed order between adjacent rows.

19. The ultrasound imaging system of claim 11, wherein the plurality of switches and the two-dimensional pattern are adapted to form a first receive aperture with a first aspect ratio and a second receive aperture with a second aspect ratio, wherein the first aspect ratio is different than the second aspect ratio.

* * * * *